(12) United States Patent
Hoffmann et al.

(10) Patent No.: US 6,770,300 B1
(45) Date of Patent: Aug. 3, 2004

(54) RAPIDLY DECOMPOSING CHITOSAN-BASED PELLETS

(75) Inventors: Hans-Rainer Hoffmann, Neuwied (DE); Bodo Asmussen, Bendorf-Sayn (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 84 days.

(21) Appl. No.: 10/069,399

(22) PCT Filed: Aug. 14, 2000

(86) PCT No.: PCT/EP00/07897
§ 371 (c)(1),
(2), (4) Date: Mar. 27, 2002

(87) PCT Pub. No.: WO01/16218
PCT Pub. Date: Mar. 8, 2001

(30) Foreign Application Priority Data

Aug. 27, 1999 (DE) .......................... 199 40 795

(51) Int. Cl.⁷ .............................. A61K 9/14; A61K 9/48
(52) U.S. Cl. ...................... 424/489; 424/451; 424/452; 424/456
(58) Field of Search ................................ 424/489, 451, 424/452, 456

(56) References Cited

U.S. PATENT DOCUMENTS 5,700,459 A * 12/1997 Krone et al. ............. 424/78.08

FOREIGN PATENT DOCUMENTS

| DE | 37 11 169 A1 | 10/1988 |
| DE | 42 01 172 C1 | 1/1992 |
| DE | 42 01 173 A1 | 7/1993 |
| DE | 42 01 179 A | 7/1993 |
| DE | 197 56 314 A | 6/1999 |
| DE | 198 45 246 A | 6/1999 |
| EP | 0 081 913 B | 6/1985 |
| JP | 01 152104 A | 6/1989 |
| WO | 98 01160 A | 1/1998 |

* cited by examiner

Primary Examiner—James M. Spear
(74) Attorney, Agent, or Firm—Birch, Stewart, Kolasch & Birch, LLP

(57) ABSTRACT

The invention relates to porous, rapidly disintegrating, active substance-containing pellets based on chitosan or a basic chitosan derivative, manufactured according to a dripping method wherein an aqueous solution or dispersion of chitosan or a basic chitosan derivative, one or more active substances, possibly further active substances and an acid is dripped into a cooling liquid having a temperature of maximally −5° C., thereby causing solidification of the solution or dispersion in the form of droplets, and wherein the solidified droplets or pellets are isolated and dried. The invention further relates to the use of these pellets in the manufacture of medicaments or diagnostic agents.

19 Claims, No Drawings

RAPIDLY DECOMPOSING CHITOSAN-BASED PELLETS

This application is the national phase under 35 U.S.C. § 371 of PCT International Application No. PCT/EP00/07897 which has an International filing date of Aug. 14, 2000, which designated the United States of America.

BACKGROUND OF THE INVENTION

1. Field of the Invention

The invention relates to the manufacture of rapidly disintegrating, particulate active substance carriers. More specifically, it relates to a process for the manufacture of porous, active substance-containing pellets for peroral application based on chitosan or a basic chitosan derivative. Furthermore, it relates to chitosan pellets obtained from this process and their use for the manufacture of medicaments and diagnostic agents.

2. Description of the Related Art

Particulate active substance carriers enjoy great popularity in pharmaceutical technology. In products intended for peroral application, they have the advantage over liquid administration forms of being lighter and more compact, possessing greater chemical stability and enabling more accurate dosage. An advantage of multiparticulate preparations such as pellets over "single units" such as tablets is the better reproducibility of their behaviour, above all when subjected to highly variable physiological conditions, since due to the large number of the administered pellets their overall behaviour develops according to statistical rules around an expected average value and the effect of individual outliers is not as great as can be the case in a tablet.

The state of the art knows a great number of carrier materials that are suitable for forming pellets. Basically, these are biocompatible substances with different chemical, physicochemical and mechanical properties. In the particular case, the selection depends on technical, economical and regulatory parameters, e.g., from the compatibility of the carrier material with the active agent(s), from the disintegration and dissolution properties, from th stability of the preparation, the raw material price, the processibility, the positive regulatory status for peroral application, etc.

Apart from pellets for preparations with controlled release of active substance, the state of the art also describes pellets with rapid-disintegration properties, which are capable of quickly releasing the active substance contained therein. Corresponding drug forms, also called acute forms, are particularly asked for in sporadically occurring indications where pharmacological action is to take place as quickly as possible. Examples are analgesics, antitussives, antiallergics, antiasthmatics, angina pectoris agents, and others. The carrier substances in such preparations are generally hydrophile or water-soluble in order to enable the desired disintegration properties. The latter are, however, also dependent on further parameters such as the presence of so-called disintegrants, i.e. substances capable of quickly absorbing water under intense swelling, or on an effective surface that is as large as possible.

Pellets having a large outer surface have a small particle size as a consequence. For a surface to be effective for the purpose of dissolution, it must be wettable, which can be ensured either by selecting the carrier material or by adding wetting agents. As an alternative, a large surface can also be due to great porosity. In that case, the particle diameter plays a rather subordinate part.

DE 42 01 172 C1 describes pellets which contain aloe vera extract as active substance and which contain gelatine or collagen as carrier, the gelatine preferably being of a cold water-soluble type.

A further carrier substance, e.g. dextrane, a sugar, sugar alcohol, glycine, or polyvinyl pyrrolidone, may also be contained. As a process of manufacture a dripping method is proposed, for instance employing the apparatus disclosed in DE 37 11 169 A1, wherein the pellets are produced by solidifying droplets in a cooling liquid, preferably in liquid nitrogen. Subsequent freeze-drying leads to the desired final product, which should possess high porosity and disintegration speed.

DE 42 01 173 A1 also discloses such pellets, but these contain a dihydropyridine derivative as active substance.

These gelatine-based cryopellets make use of the long-since known suitability of this carrier material for freeze drying to produce porous products: in Germany, for example, products of this kind for oral (e.g. Imodium® lingual, freeze-dried platelets or lamellae, by the firm of Janssen Cilag) and parenteral (e.g. Mumpsvax® dry substance) application are available on the market.

These gelatine-containing or collagen-containing preparations have the disadvantage that their success is being adversely affected by the insecurity of the population with regard to the danger of BSE contamination. Many patients or physicians prefer products without gelatine.

SUMMARY OF THE INVENTION

It is thus the object of the present invention to provide a process for the manufacture of porous, rapidly disintegrating pellets which does not require the use of gelatine, collagen or of derivatives thereof. A further object is to provide a gelatine- and collagen-free, porous, rapidly disintegrating pellets as active substance carrier for the manufacture of medicaments and diagnostic agents.

The object is achieved according to the present invention by a process for the manufacture of porous, rapidly disintegrating, active substance-containing pellets based on chitosan or a basic chitosan derivative according to a dripping method, characterized in that: a) an aqueous solution or dispersion is prepared wherein chitosan or the basic chitosan derivative, one or more active substances, an acid having a boiling point of maximally 140° C., and possibly further auxiliary substances are present predominantly in solution; b) the aqueous solution or dispersion is dripped into a cooling liquid having a temperature of maximally −5° C. and is thereby solidified in the form of droplets; c) the solidified droplets or pellets are isolated; and d) dried, and the acid is removed from the pellets.

DETAILED DESCRIPTION

It has surprisingly been found that by using a dripping method in which an aqueous dispersion with chitosan or a basic chitosan derivative is used as carrier substance and in which the other process steps are observed {i.e., a) an aqueous solution or dispersion is prepared wherein chitosan or the basic chitosan derivative, one or more active substances, an acid having a boiling point of maximally 140° C., and possibly further auxiliary substances are present predominantly in solution; b) the aqueous solution or dispersion is dripped into a cooling liquid having a temperature of maximally −5° C. and is thereby solidified in the form of droplets; c) the solidified droplets or pellets are isolated; and d) dried, and the acid is removed from the pellets}, it is possible to produce cryopellets or lyophylized pellets of a quality comparable to that of the gelatine-containing pellets described in the literature.

For the purposes of this invention, pellets are spherical or almost spherical, solid bodies having a diameter of approx. 0.1 to 6 mm. The dose unit of a pharmaceutical pellet preparation consists of a plurality of pellets. The pellets disintegrate rapidly, i.e. they are not pellets with delayed, retarded, controlled or modified release. Although the release rate is not to be equated with the disintegration rate, they nevertheless are connected with each other, so that rapidly disintegrating preparations are employed in those cases where, for the purpose of an acute form, one also aims at a quick release of active substance and a quick onset of action. Generally, such preparations break down in physiological liquids within a few minutes. The pellets are in addition porous, i.e. they possess an internal surface whose size is not negligible compared to the outer surface.

The process of manufacture according to the present invention is characterized by a sequence of a plurality of steps which can, if required, be complemented by further steps by those skilled in the art, which steps can be provided prior to, between or subsequent to the described process steps.

In a first step, an aqueous solution or dispersion is prepared, wherein chitosan or a basic chitosan derivative, one or more activ agents, possibly further auxiliary substances and an acid are present predominantly in dissolved state, i.e. their possibly undissolved portion is far smaller than their dissolved portion. This applies, in particular, to the chitosan or the basic chitosan derivative employed as carrier substance for the pellets; the use of merely suspended chitosan does not lead to suitable pellets with sufficient cohesion.

Like almost all biopolymers, chitosan, which is itself a derivative, namely a partial deacetylation product of the native polymer chitin, can be derivatized and modified in a variety of ways to alter its chemical or physicochemical properties. A basic chitosan derivative is a polymer derived from chitosan by means of a chemical, biological or physical modification process but which, like chitosan, possesses a number of positive charges. Due to the modification process, the number of positive charges can be smaller than that of the original polymer; likewise, due to the modification process negative charges may have been introduced into the molecule. For the purposes of this invention, any biocompatible chitosan derivative may be used, as long as it still has a positive overall charge or the number of the positive charges exceeds the number of negative charges. Preferred chitosan derivatives are those produced by acylation of chitosan.

Among the preferred unmodified chitosan types are those having a molar mass of more than 40,000; especially preferred are those having a molar mass above 75,000. A preferred embodiment employs unmodified chitosans with a degree of acetylation of 10 to 50%; especially preferred are acetylation degrees of 20 t 45%.

The use of chitosan or chitosan derivatives has the advantage that these are biopolymers which possess particularly good physiological tolerance and can be obtained in a simple manner from the inexpensive raw material chitin, which is availabl in large quantities, and for which a risk of BSE infection can be excluded.

While chitosan is itself largely insoluble in water, solubility markedly increases if the pH is shifted towards the acid condition. To obtain an appreciable polymer concentration, it is therefore necessary to prepare the solution or dispersion with simultaneous use of an acid. To be able to more easily remove this acid from the pellets later, it turned out that the acid should have a low boiling point, namely preferably maximally 140° C., in particular maximally 120° C., especially preferred maximally 100° C., and most preferably maximally 80° C., such as hydrogen chloride, hydrogen bromide, trifluoracetic acid, formic acid and acetic acid. Suitable are also acids forming a lower-boiling binary azeotrope with water, such as acetic acid or propionic acid. Preferably, this is a biocompatible acid; it is, however, also feasible to use a less tolerated acid, as long as it is made sure that it is later virtually completely removed from the pellets. This is more difficult with acids which boil in the region of water or higher since more drastic drying conditions must be employed which possibly lead to the product being overdried and the active substance being decomposed. For this reason, sensitive products will be dried under reduced pressure or they will be freeze-dried.

The active substance is a substance administered to produce a, in the widest sense, pharmacological effect in or on a living human or animal body. Furthermore, the term includes substances administered for diagnostic purposes.

Further pharmaceutical auxiliary agents known to those skilled in the art may also be present in the solution or dispersion. These may be, for instance, further polym r or non-polymer carrier substances, but also stabilizers, surfactants, disintegration promoters, antioxidants, dyes, pigments, flavours, sweeteners or other tast -improving agents, binders, etc.

In a further process step, the aqueous solution or dispersion is dripped into a cooling liquid having a temperature of at most −5° C. and is thereby solidified in the shape of droplets. The drops can be produced, for instance, by means of a pipette-like device, a needle or a nozzle, through which the aqueous solution or dispersion is pumped. When falling—generally through the air or a protective gas phase—the droplets assume a spherical shape, which is preserved after immersion in the cooling liquid by solidifying the ball-shaped or almost ball-shaped droplets. Depending on various parameters known to those skilled in the art, e.g. the density and the viscosity of the aqueous phase, the shape, the diameter and the interfacial tension at the dripping device, etc., the droplets can be produced in different sizes. Preferred are those embodiments in which droplets of 0.3 to 5 mm in diameter are formed. The size of the droplets contributes decisively to the particle size of the pellets obtained from the process, although the two sizes are not to be equated. As a rule, the modal droplet size will be somewhat larger than the modal pellet diameter.

To produce immediate solidification, the temperature of the cooling liquid must be clearly below 0° C., and for the purposes of the invention must be −5° C. at maximum. An embodiment of the invention using a cooling liquid with a temperature of less than −15° C. is preferred. Especially preferred are cooling liquids which are freeze-dried, inert, liquefied gases or mixtures of gases, e.g. liquid air or liquid nitrogen. Such an embodiment is most likely to ensure immediate solidification of the aqueous solution or dispersion upon immersion in the cooling liquid.

Coolants of this kind can in addition be removed from the product specially easily and virtually completely.

In a further process step the solidified droplets, which are now pellets, are isolated. This can take place in various ways, depending on the configuration of the dripping and cooling apparatus employed. A simple possibility is to pass the pellets-containing cooling fluid through a strainer. During this process, the pellets can simultaneously be classified. Pellets according to the invention which are produced by the described process possess a particle size from about 0.3 to 5 mm. Preferred pellet diameters are 0.8 to 3 mm.

In a further process step, the thus-isolated pellets are dried. Because of the high water content, a temperature of around 0° C. should not be exceeded when isolating and drying under normal pressure conditions. However, it is recommendable and preferred according to the present invention to perform freeze-drying at reduced pressure, which enables the removal of water from the pellets also at slightly higher temperatures, through sublimation, and through which a highly porous pellet structure can be obtained. Appropriate apparatuses and process parameters are known to those skilled in the art.

The invention, apart from the disclosed process of manufacture, also relates to the pellets produced by the process. Corresponding to what is said above, these are spherical, porous, rapidly disintegrating, and preferably have a particle size of 0.3 to 5 mm in diameter, especially preferred 0.8 to 3 mm. Their composition is in addition selected such that in a preferred embodiment they possess a surface charge which can b express d as z ta potentials from +0.5 to +50 mV. This surface charge is due to the fact that the pellets are substantially based on the carrier substance chitosan or a basic chitosan derivative.

For greater ease of handling and better applicability of the pellets, these can be present filled in doses in hard gelatine capsules or comparable hard capsules of starch or other polymers. While hard gelatin. capsules are commonly used for administration of pellets, it may be appropriate to select another capsule material, such as starch, on account of the above-mentioned BSE problem, which does not affect the pellets themselves.

As an alternative to administration as hard capsule, application as instant preparation is also possible. In this case, the pellets—which are provided in a multiple dose container, or in doses packed in sachets—can be introduced in water or another liquid, in which they disintegrate forming a ready-to-drink preparation. For such an application purpose, but also for filling into hard capsules, it may be necessary to mix the pellets according to the present invention with further auxiliary substances that have an influence, for example, on the flowability, adhesion tendency, stability, etc., of the pellets. In this respect, the use of the pellets in accordance with the present invention includes any kind of further processing to yield a medicament or a diagnostic agent.

What is claimed is:

1. A process for the manufacture of porous, rapidly disintegrating, active substance-containing pellets based on chitosan or a basic chitosan derivative according to a dripping method, which comprises:
    a) preparing an aqueous solution or dispersion, wherein chitosan or the basic chitosan derivative, one or more active substances, an acid, having a boiling point of maximally 140° C., and possibly further auxiliary substances are present predominantly in solution,
    b) dripping the aqueous solution or dispersion into a cooling liquid having a temperature of maximally −5° C. and is thereby solidified in the form of droplets;
    c) isolating the solidified droplets or pellets; and
    d) drying, and the acid is removed from the pellets.

2. The process according to claim 1, wherein the drying of the isolated pellets is carried out by means of a freeze-drying process.

3. The process according to claim 1, wherein the cooling liquid has a temperature of less than −15° C.

4. The process according to claim 1, wherein the cooling liquid is a liquefied gas or a liquefied gas mixture.

5. The process according to claim 1, wherein the cooling liquid is liquid air or liquid nitrogen.

6. The process according to claim 1, wherein the droplet size is 0.3 to 5 mm in diameter.

7. The process according to claim 1, wherein the chitosan or chitosan derivative employed has a molar mass of more than 40,000.

8. The process according to claim 1, wherein the chitosan or chitosan derivative used has a molar mass of more than 75,000.

9. The process according to claim 1, wherein the chitosan or chitosan derivative used has an acetylation degree of 10 to 50%.

10. The process according to claim 1, wherein the chitosan or chitosan derivative employed has an acetylation degree of 20 to 45%.

11. The process according to claim 1, wherein the basic chitosan derivative is an acylated chitosan.

12. Porous active substance-containing pellets which disintegrate in physiological liquids within several minutes and are based on chitosan or a basic chitosan derivative, wherein the pellets are manufactured by means of a process according to claim 1.

13. The porous rapidly disintegrating, active substance-containing pellets according to claim 12, wherein they have a zetapotential of +0.5 to +50 mV.

14. The porous rapidly disintegrating, active substance-containing pellets according to claim 12, wherein they have an average particle size of 0.3 to 5 mm in diameter.

15. The porous rapidly disintegrating, active substance-containing pellets according to claim 12, wherein they have an average particle size of 0.8 to 3 mm in diameter.

16. The porous rapidly disintegrating, active substance-containing pellets according to claim 12, wherein for purposes of application they are present in a hard capsule.

17. The porous rapidly disintegrating, active substance-containing pellets according to claim 12, wherein prior to intake they are placed in a liquid in which they disintegrate.

18. A medicament which comprises the pellets according to claim 12.

19. A diagnostic agent that comprises the pellets according to claim 12.

* * * * *